United States Patent
Back et al.

(10) Patent No.: US 10,800,962 B2
(45) Date of Patent: Oct. 13, 2020

(54) FORMULATIONS FOR ENHANCED OIL RECOVERY COMPRISING SULFONATES

(71) Applicant: RHODIA OPERATIONS, Paris (FR)

(72) Inventors: Olivier Back, Lyons (FR); Remy Leroy, Vaulx En Velin (FR); Mikel Morvan, Pessac (FR); Patrick Moreau, Bordeaux (FR); Philippe Marion, Vernaison (FR)

(73) Assignee: RHODIA OPERATIONS, Paris (FR)

( * ) Notice: Subject to any disclaimer, the term of this patent is extended or adjusted under 35 U.S.C. 154(b) by 111 days.

(21) Appl. No.: 15/572,401

(22) PCT Filed: May 4, 2016

(86) PCT No.: PCT/EP2016/060070
§ 371 (c)(1),
(2) Date: Nov. 7, 2017

(87) PCT Pub. No.: WO2016/177817
PCT Pub. Date: Nov. 10, 2016

(65) Prior Publication Data
US 2018/0119002 A1  May 3, 2018

(30) Foreign Application Priority Data
May 7, 2015 (EP) .................... 15305707

(51) Int. Cl.
C09K 8/584 (2006.01)
C07C 309/07 (2006.01)
E21B 43/16 (2006.01)
(52) U.S. Cl.
CPC ............ C09K 8/584 (2013.01); C07C 309/07 (2013.01); E21B 43/16 (2013.01)
(58) Field of Classification Search
None
See application file for complete search history.

(56) References Cited

U.S. PATENT DOCUMENTS

| | | | |
|---|---|---|---|
| 3,819,691 A | 6/1974 | Kurkov et al. | |
| 4,022,699 A * | 5/1977 | Holm | C09K 8/584 507/259 |
| 4,784,790 A * | 11/1988 | Disch | A61B 1/121 422/20 |
| 5,223,166 A * | 6/1993 | Disch | A61B 1/121 510/161 |
| 2013/0143787 A1* | 6/2013 | Siegert | C11D 3/221 510/393 |

FOREIGN PATENT DOCUMENTS

DE  4220580 A1  1/1994
WO  2014193720 A1  12/2014

OTHER PUBLICATIONS

Derwent Abstract of DE 4220580 A1 to Raths et al, published Jun. 13, 1994. (Year: 1994).*

* cited by examiner

*Primary Examiner* — John J Figueroa

(57) ABSTRACT

Compositions suitable for enhanced oil recovery comprising a) a mixture of a-sulfocarbonyl compounds of formula (1) and (2) in a mixture ratio (1) to (2) of from 1:99 to 99:1 wherein $R_1$, $R_3$ and $R_5$, which may be the same or different at each occurrence, are hydrogen or a linear or branched alkyl chain having 1 to 20 carbon atoms, $R_2$ and $R_4$, which may be the same or different at each occurrence, may be a linear or branched alkyl group having 4 to 24 carbon atoms and in which the alkyl chain may comprise one or more cycloaliphatic groups, and X is H or a metal forming a salt with the sulfonate group, and b) a salt containing aqueous solution.

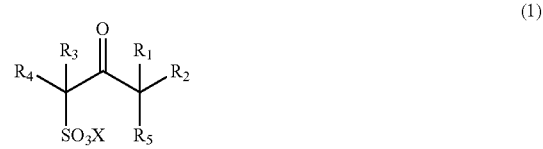

(1)

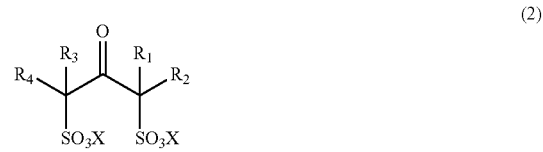

(2)

3 Claims, No Drawings

FORMULATIONS FOR ENHANCED OIL RECOVERY COMPRISING SULFONATES

This application is a U.S. national phase entry under 35 U.S.C. § 371 of International Application No. PCT/EP2016/060070, filed on May 4, 2016, which claims priority to European Application No. 15305707.0, filed on May 7, 2015. The entire content of these applications is being incorporated herein by this reference.

The present inventions relates to compositions for enhanced oil recovery.

Oil recovery from natural oil reservoirs provides the word economy with the necessary fuel and raw materials for a vast number of processes and products.

Generally, three different techniques are used for recovering oil from natural reservoirs.

During primary recovery the natural pressure of the reservoir or gravity drive oil into the well bore, combined with artificial lift techniques such as pumps which bring the oil to the surface. Only about 10% of the oil content of the reservoir are usually produced during primary recovery.

Secondary recovery techniques extend the reservoirs productive life generally by injecting water or gas to displace the oil and drive it to a production wellbore which ultimately results in the recovery of approximately 20 to 40% of the original oil in place.

In view of the fact that much of the easy to produce oil recoverable by primary or secondary recovery has been exploited with leaving on average 60% or more of the original oil remaining in the reservoir, oil producers are interested in enhanced oil recovery techniques which offer the perspective for ultimately exploiting a higher percentage of the original oil content of the oil reservoir. These techniques are summarized in the term Enhanced Oil Recovery (hereinafter referred to as EOR) or tertiary oil recovery.

Three major categories of EOR have been found to be commercially successful to varying degrees.

Thermal recovery involves the introduction of heat such as the injection of steam to lower the viscosity of the heavy viscous oil and improve its ability to flow through the reservoir.

Gas injection, which uses gases such as natural gas, nitrogen or carbon dioxide that expand in a reservoir to push additional oil to a production wellbore or other gases that dissolve in the oil to lower its viscosity and improves the flow rate is the second method.

The third method is often referred to as chemical oil recovery and involves the use of certain chemical compounds or compositions to increase the effectiveness of water floods or the use of detergent-like surfactants to help lower the interfacial tension between the crude oil in the reservoir and the injected brine which often prevents oil droplets from moving through a reservoir.

Whereas in a fresh oil reservoir the oil is present as a continuous phase in the rock formation, this continuous oil phase disintegrates with increasing primary and secondary recovery leaving the oil in discrete droplets which are retained in narrow pores under the effect of high interfacial tension. Overcoming the capillary forces requires either a high pressure or a very considerable reduction in the interfacial tension between water and oil which is targeted through the use of surfactants. The reduction of interfacial tension achievable depends on a variety of different influencing factors such as reservoir temperature, salinity of the reservoir water and composition of the oil itself.

U.S. Pat. No. 5,318,709 relates to surfactant mixtures based on ether sulfonates and their use in EOR. These surfactant mixtures are suitable for use in so-called surfactant flooding. The process comprises preparing a surfactant mixture consisting essentially of an alkyl ether sulfonic acid or salt thereof as a principal constituent and at most a substantially equal quantity of alkoxylated alcohol as a by-product of the process.

DE 42 20 580 relates to α-sulfocarbonyl compounds obtained by heating fatty ketones or fatty aldehydes which are liquid below temperatures of 90° C. with gaseous sulfur trioxide and subsequent neutralization of the reaction products with an aqueous base. The products are said to be suitable for the manufacture of surface active agents.

GB 1,236,203 relates to new surface active compounds and their preparation. According to the process claimed a paraffin hydrocarbon having from 10 to 30 carbon atoms is oxidized with molecular oxygen to obtain a mixture of secondary alcohols and ketones. The mixture is optionally purified to concentrate the ketones and thereafter the ketones are reacted with a sulfonating agent followed by neutralization with a base to obtain a mixture comprising water soluble salts of sulfonated ketones. Mixtures comprising substantially non-symmetrical sulfonated dialkyl ketone salts having from 10 to 30 carbon atoms in the molecule chain are also claimed. The products are said to be valuable as surface-active, wetting and emulsifying agents and therefore may be used in a variety of applications.

U.S. Pat. No. 2,195,088 relates to sulfonated ketones which are obtained by the direct sulfonation of internal ketones with long alkyl chains of at least six carbon atoms. The sulfonated ketones are said to be resistant to hard water, acids and alkalies and to provide products with good wetting, emulsifying, dispersing and cleansing action.

WO 2015/017850 relates to a method for recovering hydrocarbons from a geological structure which method comprises injecting a composition into the geological structure, wherein the composition comprises a partially sulfonated polymer, wherein the partially sulfonated polymer comprises a polymer chain comprising a plurality of monomer units, wherein the monomeric units comprise sulfonated monomer units associated with sulfonated moieties, and unsulfonated monomeric units that do not contain the sulfonated moiety.

There is an ongoing need for compositions suitable for enhanced oil recovery which can be fine tuned according to the specific situation in the reservoir in the geological structure as e.g. salinity of the reservoir water, adjustment of interfacial tension and satisfactory solubility in the stream to be injected.

It was thus an object of the present invention to provide compositions suitable for use in enhanced oil recovery techniques which overcome the disadvantages of the prior art described above and allow the easy adjustment of the properties of the composition to the specific situation of a given operation.

This object has been achieved with the competition in accordance with claim 1.

Preferred embodiments of the present invention are set forth in the dependent claims and the detailed specification hereinafter.

The compositions in accordance with the present invention comprise as component a) a α-sulfocarbonyl compounds mixture of mono- and disulfonated internal ketones with long chain alkyl groups with a mixture ratio of monosulfonate:disulfonate of from 1:99 to 99:1, preferably of from 3:97 to 97:3 and even more preferably in the range of from 5:95 to 95:5.

The sulfonates comprise sulfonate groups at the α-carbon atom relative to the carbonyl group of the internal ketone. Whereas monosulfonates comprise one sulfonate group at one of the carbon atoms in α-position to the carbonyl group, disulfonates comprise two sulfonate groups, one at each of the α-carbon atoms relative to the carbonyl group. Accordingly, monosulfonates may be generally characterized by formula (1) and disulfonates may be generally characterized by formula (2) below

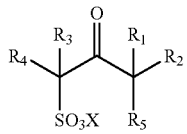

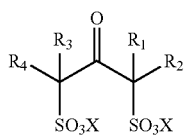

wherein $R_1$, $R_3$ and $R_5$, which may be the same or different at each occurrence, are hydrogen or a linear or branched alkyl chain having 1 to 20 carbon atoms, $R_2$ and $R_4$, which may be the same or different at each occurrence, may be a linear or branched alkyl group having 4 to 24 carbon atoms and in which the alkyl chain may comprise cycloaliphatic groups, and X is H or a cation forming a salt with the sulfonate group and b) a salt containing aqueous solution.

Preferred cations X are selected from the group consisting of ammonium and metal cations. e.g. sodium, potassium, calcium and magnesium.

Preferably, $R_1$, $R_3$ and $R_5$ are hydrogen or an alkyl group having of from 1 to 6 carbon atoms, particularly preferred hydrogen, methyl, ethyl, propyl, butyl, pentyl or hexyl, with hydrogen being most preferred.

$R_2$ and $R_4$ preferably comprise 6 to 18 and even more preferably 6 to 14 carbon atoms.

If $R_2$ and or $R_4$ are linear or branched alkyl chains, and in particular linear alkyl chains, the sulfonates can be obtained by the sulfonation of internal ketones obtained from fatty acids or fatty acid mixtures or derivatives of fatty acids or their mixtures.

Preferred fatty acids from which the internal ketones are derived are caprylic acid, capric acid, lauric acid, myristic acid, palmitic acid, stearic acid, arachidic acid, behenic acid, lignoceric acid, cerotic acid or mixtures thereof and preferred acid derivatives are the esters and anhydrides of these acids. Preferred are caprylic acid, capric acid, lauric acid, myristic acid, palmitic acid, stearic acid, naphthenic acids, isostearic acids or mixture thereof. Preferably the starting fatty acids mixture is in the form of the so-called cuts which are obtained from vegetable or animal oils through saponification or alcoholysis. More preferably the fatty acids cut is derived from coconut oil or palm kernel oil and contains a mixture of fatty acids which can comprise fatty acids having 8 carbon atoms up to 18 carbon atoms. Internal ketones can also be obtained through cross-ketonization reactions starting from a mixture of linear fatty acids and naphthenic acids.

The fatty acids or fatty acid derivatives from which the internal ketones are derived may also comprise one or more double bonds in the chain like oleic acid, linoleic acid, linolenic acid or erucic acid to name only a few examples. However, since the double bonds in such fatty acids during the sulfonation are also sulfonated, the reaction products after sulfonation constitute a less well defined mixture as molecules with more than two sulfonate groups and with the sulfonated groups located in various positions of the main chain of the molecule may be formed. Accordingly, it is preferred to use internal ketones derived from saturated fatty acids to avoid these complications.

The internal ketones which are subjected to the sulfonation may also be partially or entirely derived from so called naphthenic acids. The term naphthenic acid generally denotes an unspecific mixture of cyclopentyl and cyclohexyl carboxylic acids with a carbon backbone of usually 9 to 20 carbon atoms. Naphthenic acids are obtained by oxidation of the naphtha fraction of crude oil and their composition varies with the crude oil composition and the conditions during refining and oxidation.

The sulfonates represented by formulae (1) or (2) may be obtained from one single internal ketone which may be derived from one single acid or acid derivative or it may be derived from a mixture of different internal ketones which may be obtained from acids or acid derivatives with a different chain length for $R_1$ to $R_5$ such as e.g so called fatty acid cuts.

The mixture ratio in case of a mixture of ketones being used for the sulfonation is not subject to any particular limitation.

The sulfonates can be obtained by sulfonation of the respective internal ketones with a sulfonating agent.

The sulfonating agent is advantageously selected from sulfuric acid, sulfuric acid monohydrate, oleum, chloro sulfonic acid, sulfonic acid or gaseous sulfur trioxide. Besides, it is advantageously used in a concentrated form.

In accordance with a first preferred alternative the sulfonation to obtain the desired sulfonates can be carried out using a falling film reactor, including a laboratory scale falling film reactor. This reactor may be equipped with a cooling jacket supplied with cold water in order to prevent temperature increases in the reactor due to the high exothermicity of the reaction. For this reaction, the temperature of the cooling jacket is usually set-up at around 0° to 8 C. The reaction temperature in the reactor is usually in the range of from 50 to 110° C., preferably of from 65 to 100° C. and even more preferably in the range of from 70 to 90° C.

A gas flow consisting of a mixture of sulfonating agent (e.g. anhydrous $SO_3$) diluted with carefully dried inert gas (e.g. nitrogen or air) at a concentration usually in the range of from 0.5 to 10, preferably of from 1 to 5% v/v (particularly preferred around 2.5% v/v) is contacted with a falling film of liquid internal ketone. The flows of gas and liquid phases are set-up in order to ensure a residence time of from 10 seconds to 10 min, preferably of from 1 min to 6 min (e.g. 3 minutes) in the reactor and a molar ratio $SO_3$:Internal ketone in the range of from 0.3:1 to 3:1, preferably of from 0.4:1 to 2.5:1 and most preferably of from 0.5:1 to 2.1:1.

When using a mixture of internal ketones with different chain lengths (and thus different molecular weights) the total molar flow of internal ketones can be calculated using the average molecular weight of the mixture of ketones.

Following the sulfonation reaction the mixture exiting the reactor (composed mainly of monosulfonic acid and disulfonic acids) can be allowed to age in order to allow trans-sulfonation to occur and to increase the conversion of starting ketones.

Thereafter, the obtained mixture can be neutralized using an aqueous solution of a base (e.g. NaOH) in a suitable reactor preferably in a batch mode in a reactor equipped with a mechanical stirring. Neutralization is then carried out by heating the mixture under mechanical stirring. During this stage of the process, the sulfonic acids are transformed into to desired Internal Ketone Sulfonates through a deprotonation reaction. The reaction temperature during the neutralization is usually in the range of from 40 to 100° C., preferably in the range of from 50 to 80° C. and the reaction time may vary but in many cases is in the range of from 30 min to 5 h, preferably 40 min to 3 h.

According to a second preferred method the sulfonation may be carried out in a (batch) reactor equipped with a mechanical stirring in the liquid phase using an in-situ prepared sulfonating reagent, e.g. "$SO_3$-dioxane" complex or a chlorosulfonic acid/dioxane complex.

In a round bottom flask anhydrous dioxane (1 molar equivalent with respect to the amount of the sulfonating agent used) and anhydrous trichloromethane (dioxane/$CHCl_3$ mixture ratio 1:2 to 1:5 v/v) are mixed and cooled down to a temperature in the range of from −5 to 10° C., preferably to about 0° C. Then the sulfonating agent (liquid $SO_3$ or chlorosulfonic acid in the desired amount) is slowly added under stirring during 10 minutes to generate the complex $SO_3$-dioxane or $ClSO_3H$-dioxane.

This sulfonating agent containing solution is then carefully added to the solution of the fatty ketone in trichloromethane (ketone concentration in the range of from 0.1 g/mL to 1 g/mL) maintained preferably at 45° C. during a period of from 0.3 hour to 3 hour, preferably during appr. 1 hour and through four crops. After addition completion, the mixture is allowed to stir at a temperature of from 30° C. to 100° C., preferably from 45° C. to 65° C., during a period of from 0.5 hour to 3 hours, and preferably during appr. 1 hour. During this time the color of the mixture changes from light yellow to dark brown. All the volatiles ($CHCl_3$ and dioxane) are then removed under vacuum and the residue is neutralized with an aqueous solution of a base (e.g. NaOH) using same procedure as in [0039]

The sulfonation, digestion and neutralization reactions can be followed using NMR analysis. At the end of the process the amount of water in the medium may be adjusted in order to reach an aqueous solution of Internal Ketone Sulfonates with a desired concentration of active matter.

If the sulfonating agent is used in a less than equimolar amount, unreacted free ketones remain in the reaction mixture which for some applications should be removed. This ketone can be separated from the aqueous sulfonate mixture using conventional techniques such as: filtration, decantation at a temperature where the ketone is melted (80° C. and below 100° C.), washing the aqueous solution with organic non polar solvent which is not miscible with water such as toluene or flash chromatography on silica gel using $CHCl_3$ followed by $CHCl_3$:MeOH (90:10) mixture as eluent.

It has been found that the ratio of monosulfonic acid (or sulfonate after neutralization) to disulfonic acid (or disulfonate after neutralization) can be controlled through appropriate selection of the molar ratio of sulfonating agent and internal ketone. If a molar ratio of 0.5:1 or less is used, the reaction product comprises basically only the monosulfonate (yield more than 90%), whereas at a molar ratio of 1.5:1, the reaction product contains almost equivalent amounts of monosulfonate/disulfonate (appr. 50/50 in mol %) and at a molar ratio of 2:1 or higher the disulfonate is obtained in more than 90% yield.

In the course of the invention it has been found that the ratio of monosulfonate:disulfonate in the mixture can be used as a parameter to tune the properties of the compositions of the present invention to optimize same for a given salinity of the reservoir water and to achieve the desired low interfacial tension.

The optimal salinity corresponds to the salinity at which the interfacial tension of the composition in accordance with the present invention with the oil reaches its minimum value. By modifying the ratio monosulfonate/disulfonate the solubility of the sulfonates in the reservoir water can be optimized to achieve the best results in the enhanced oil recovery process. For a given salinity of the brine or reservoir water there exists a molar ratio of monosulfonates to disulfonates which yields the lowest interfacial tension. As a general rule a higher salinity of the brine or reservoir water requires a higher amount of disulfonates in the compositions to achieve the optimum result. Increasing the amount of disulfonate also increases the solubility of the mixture of sulfonates in the aqueous salt solution thereby also contributing to optimum results in the final process. This enables the compositions of the present invention to be used for enhanced oil recovery with reservoirs having a widely differing salinity of the brine or reservoir water.

The compositions in accordance with the present invention contain, as component b) a salt containing aqueous solution. Usually this aqueous salt solution corresponds in its salt content to the salt content of the reservoir water in the underground or it is such reservoir water. Using reservoir water or an aqueous solution the salt content of which equals the salt content of the reservoir water allow to adjust the amounts of the components in the composition and in particular the ratio of monosulfonate and disulfonate in the sulfonate mixture in such a way to achieve the best oil recovery if the composition is used for the so-called surfactant flooding enhanced oil recovery. As explained before the ratio of monosulfonate to disulfonate should be chosen dependent on the salinity of the brine or reservoir water used as component b).

The salt content of the aqueous solution b) is normally in the range of from 1 to 200 g/L, preferably in the range of from 5 to 150 g/L, expressed as total salt content.

The salts present in the aqueous solution b) are normally halides of group I or group II metals, such as. NaCl, KCl, RbCl, CsCl, MgCl, BeCl2, CaCl2 to name only a few examples. The composition may and usually will contain more than one type of salt and the salt content is always given with regard to the overall amount of salt in the composition.

The weight ratio of component a) and component b) in the composition of the present invention is not particularly critical and can vary over a wide range.

The aqueous salt solution or brine (component b) normally constitutes the major constituent of the compositions in accordance with the present invention and the sulfonate mixture (component a) is the minority component in the composition.

In certain cases concentrations of sulfonate mixture of from 0.5 to 50 g/L of the aqueous salt solution, preferably of from 1 to 30 g/L and particularly preferably of from 2 to 20 g/L have shown to be effective.

The compositions in accordance with the present invention may, in addition to components a) and b) described hereinabove, contain additional components which may contribute to achieve the best in on recovery results upon use.

Thus, e.g. further surface active compounds may be present in the compositions. Just by way of example nonionic surfactants may be mentioned here, such as alkoxylated nonyl phenol, alkoxylated dinonylphenol, and alkoxylates of various straight and branched alcohols having a carbon chain of preferably from 8 to about 20 or more carbon atoms may be mentioned here. These additional surface active components may also be carboxylated, phosphated, sulfated or sulfonated, i.e. ionized upon use.

A preferred group of additional hydrophilic surfactants which may be present in the compositions in accordance with the present invention are alkyl glyceryl ether sulfonates (AGES). Alkyl glyceryl ether sulfonates (AGES) are well known as detergents utilized in personal care cleansing products and are commercially available from a number of sources. The skilled person will select the best suited AGES based on his professional experience and adapted to the specific case of use so that no further details needs to be given here.

Processes for the manufacture of AGES are described in U.S. Pat. Nos. 3,024,273 and 2,989,547 to which reference is made herewith for further details.

Alkyl glyceryl ether sulfonate salts can be represented by the general formula

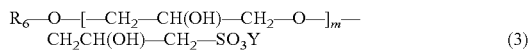

$$R_6-O-[-CH_2-CH(OH)-CH_2-O-]_m-CH_2CH(OH)-CH_2-SO_3Y \quad (3)$$

wherein $R_6$ represents a linear or branched alkyl or alkenyl chain having of from 3 to 32 carbon atoms, preferably of from 5 to 18 carbon atoms. m is 0 or an integer in the range of from 1 to 20, preferably of from 2 to 15 and Y is a cation selected from the group consisting of sodium, potassium, ammonium, calcium or magnesium.

It is easily apparent that for m being 0 the product is the sulfonate of an alkyl glyceryl ether.

Another group of preferred surfactants useful in combination with the internal ketone sulfonates in the compositions of the present invention is alkoxylated alkyl glyceryl ether sulfonates (AAGES) which differ from the alkyl glyceryl ether sulfonates described above by the presence of one or more alkoxy groups between the last carbon atom of the article group and the oxygen atom of the alkyl glyceryl ether sulfonate. AAGES may be represented by the following general formula:

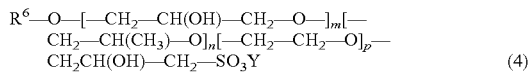

$$R^6-O-[-CH_2-CH(OH)-CH_2-O-]_m[-CH_2-CH(CH_3)-O]_n[-CH_2-CH_2-O]_p-CH_2CH(OH)-CH_2-SO_3Y \quad (4)$$

wherein $R_6$, m and Y may have the meaning as defined before and n and p are integers of from 0 to 20, preferably of from 2 to 15 and n and p cannot be both equal to 0.

If present, AGES or AAGES may be used in a concentration of from 0.5 to 50 g/L, preferably of form 1 to 25 g/L of aqueous salt solution b). Preferably, in case of a combination of component a) and AGES or AAGES, both components are used in in a weight ratio of preferably of from 1:10 to 10:1, preferably of from 1:5 to 5:1.

The compositions in accordance with the present invention can contain additional ingredients which are customary ingredients of surfactant flooding compositions for enhanced oil recovery processes.

The way of use of the compositions of the present invention in enhanced oil recovery processing is known to the skilled person and has been described in the literature so that no further details need to be given here. The skilled person will decide on the best process based on his professional experience and taking into account the specific circumstances of the individual application case.

A further embodiment of the present invention relates to a process for enhanced oil recovery wherein in a first step the salinity of the injection water is determined and thereafter a blend of internal ketone monosulfonates and disulfonates as defined in claim 1 is prepared having a mixing ratio of mono- and disulfonates providing the lowest interfacial tension with the crude oil for the given salinity, mixing the internal ketone sulfonate mixture with the injection water and optionally further ingredients and pumping the final composition into the reservoir to recover oil from the reservoir. The best suitable mixing ratio for a given salinity can be determined through a series of simple experiments with different molar ratios of mono- and disulfonates.

Another embodiment relates to compositions comprising a mixture of component a) and an AGES of formula (3) or an AAGES of formula (4) or mixtures thereof.

The compositions in accordance with the present invention provide efficient solutions for enhanced oil recovery.

EXAMPLES

Example 1—Synthesis of 12-tricosanone

Examples 1 and 2 show a preferred process for the manufacture of internal ketones which are the starting material for the internal ketone sulfonates used in the compositions of the present invention.

The reaction was carried under argon in a round bottom flask equipped with mechanical stirring, Dean Stark apparatus and an addition funnel. In the reactor, 700 mg of iron powder were dispensed and 20 g of lauric acid was introduced into the addition funnel.

A first partial amount of 5 g of acid was added into the reactor and the temperature was brought to 250° C. The mixture was stirred at this temperature for 30 minutes during which the color of the media changed to black and $H_2$ gas was released.

Then the temperature was raised to 300° C., the mixture was stirred during 1 h 30 and the remaining amount of lauric acid (15 grams) was slowly added into the reactor during 4 h 30 min at a flow rate which allowed keeping concentration of lauric acid in the reaction media very low (no accumulation of free acid in solution).

At the end of the reaction, the addition funnel was replaced by a distillation apparatus and the products were distilled off at 290° C.-340° C. under 5 kPa pressure.

Overall 4 cycles were carried out without any loss of performances reducing thereby the concentration of iron to less than 1 wt % relative to fatty acids amount converted.

The conversion, selectivity and yield (measured by gas chromatography (GC) and isolated) are given in Table 1 below.

TABLE 1

(all values in % of theory)

| Cycle no. | Conversion | Selectivity | Raw yield | Isolated yield |
|---|---|---|---|---|
| 1 | 100 | 90 | 90 | 77 |
| 2 | 100 | 89 | 89 | 70 |
| 3 | 100 | 87 | 87 | 85 |
| 4 | 100 | 89 | 89 | 87 |

The data show the superior selectivity and yield of the desired ketone.

Example 2—Cut of Coco Fatty Acids as Starting Material for the Synthesis of Internal Ketones Conversion of 400 g of coco fatty acids having the following weight distribution: $C_{12}$: 55%, $C_{14}$: 21%, $C_{16}$: 13%, $C_{18}$: 12%.

The transformation was carried out using 6.4 g of iron powder (1.6 wt %) and through 2 cycles involving a total of 200 g of fatty acids for each cycle.

The reaction was carried under argon in a 1 l round bottom flask equipped with mechanical stirring, Dean-Stark apparatus and an addition funnel.

Into the 250 mL addition funnel 200 g of coco fatty acids were introduced which were maintained in molten form by an external heater.

6.4 g of iron powder were dispensed into the reactor and a first portion of fatty acids (around 58 mL) were added into the reactor. The mixture was stirred (500 rpm) at 250° C. during 30 minutes in order to convert metallic iron to iron salts. During this period, the mixture color changed to black and hydrogen was released. Then the temperature was raised to 300° C.-320° C. to perform the transformation to fatty ketones. The mixture was stirred at this temperature during 1 h 30 and the remaining part of fatty acids was slowly added in the reactor during 5 hours at a flow which allowed keeping a low concentration of fatty acids in solution (no accumulation of free acids in solution). At the end of the reaction, the addition funnel was replaced by a distillation apparatus and the fatty ketones were recovered by distillation (290° C.-340° C., 5 kPa).

A first crop of 141 g of fatty ketone was recovered as a white wax.

The residue left in the reactor flask and mainly constituted of iron salts was used to convert the remaining 200 g of fatty acids in a second cycle. To achieve this, the distillation apparatus was replaced by the addition funnel containing 200 g of molten fatty acids and the operational steps described above were repeated.

The total yield of the reaction after these 2 cycles was: 79% isolated as a white wax.

Example 3—Sulfonation of 12-tricosanone (Obtained in Example 1) with 0.5 Moles of Sulfonating Agent Per Mol of Ketone The reactions were performed under a strictly anhydrous argon atmosphere. All the glassware was dried under vacuum at 110° C. overnight prior to the reaction. In a 100 mL round bottom flask equipped with a mechanical stirring, 10 g (29.5 mmol) of 12-tricosanone was dissolved in 27 mL of $CHCl_3$ and the temperature of the mixture was set up at 45° C.

In another round bottom flask, a solution of 1 mL of $ClSO_3H$ (14.5 mmol) dissolved in 5 mL of $CHCl_3$ and 1.2 mL of dioxane (14.5 mmol) was carefully prepared. This solution was then slowly added to the ketone solution via cannula over 1 hour and through 4 crops in order to prevent disulfonation to occur in significant amounts. After addition, the mixture was allowed to stir at 60° C. during 1 hour and the solvent was removed under vacuum. Then the sulfonic acid was neutralized with 6.4 mL NaOH (10 wt %) along with an additional amount of 12 mL of water and under mechanical stirring at 60° C. during 1 hour in order to afford sodium sulfonate salts. The starting ketone in excess was finally separated from the monosulfonate after water evaporation, through filtration over silica (50 g) and elution with dichloromethane followed by $CH_2Cl_2$/MeOH (90:10). After evaporation of the solvent 4.1 g of white solid was obtained corresponding to 64% of isolated yield. As determined through NMR analysis, the product consisted of a mixture of 95 mol % monosulfonate and 5 mol % disulfonate.

Example 4—Sulfonation of 12-tricosanone (Obtained in Example 1) WITH 1.5 Moles of Sulfonating Agent Per Mol of Ketone The reaction was performed as described above for Example 2 except that an excess of 1.5 eq (43.5 mmol) of $ClSO_3H$ (and 1.5 eq of dioxane) was reacted with 1 eq of 12-tricosanone (29.5 mmol). Quantities of solvent $CHCl_3$ were also adjusted.

Neutralization of sulfonic acids was carried out using 1.1 eq of NaOH (10 wt %) (calculated with respect to $ClSO_3H$ amounts) in water at 60° C. during 1 hour.

No further purification was needed as under those conditions all the starting ketone was consumed. After neutralization, the obtained mixture of sulfonated salts (35 wt % active matter in water) could be used as such for the preparation of the compositions of the present invention.

After evaporation of the water, 15 g of white solid is obtained corresponding to a quantitative isolated yield.

As determined through NMR analysis, the product consisted of a mixture of 52 mol % monosulfonate and 48 mol % disulfonate.

Example 5—Sulfonation of Ketones Obtained in Example 2 With 0.5 Moles of Sulfonating Agent Per Mol of Ketone The reactions were performed under a strictly anhydrous argon atmosphere. All the glassware was dried under vacuum at 110° C. overnight prior to the reaction. In a 250 mL round bottom flask equipped with a mechanical stirring, 40 g (106.5 mmol) of internal ketones obtained in accordance with Example 2 was dissolved in 107 mL of $CHCl_3$ and the temperature of the mixture was set up at 45° C.

In another 50 mL round bottom flask, a solution of 3.8 mL of $ClSO_3H$ (56.5 mmol) dissolved in 17 mL of $CHCl_3$ and 4.8 mL of dioxane (56.5 mmol) was carefully prepared. This solution was then slowly added to the ketone solution via cannula over 1 hour and through 4 crops in order to prevent disulfonation to occur in significant amounts. After addition, the mixture was allowed to stir at 60° C. during 1 hour and the solvent was removed under vacuum. Then the sulfonic acid was neutralized with 37.4 mL aqueous NaOH (10 wt %) under mechanical stirring at 60° C. during 1 hour in order to afford sodium sulfonate salts. The starting ketone in excess was finally separated from the monosulfonate salt after water evaporation, through filtration over silica (250 g) and elution with dichloromethane followed by $CH_2Cl_2$/MeOH (90:10). After evaporation of the solvent 19.4 g of white solid was obtained corresponding to 57% of isolated yield. As determined through NMR analysis, the product consisted of a mixture of 96 mol % monosulfonate and 4 mol % disulfonate.

Example 6—Sulfonation of Ketones Obtained in Example 2 with 1.5 Moles of Sulfonating Agent Per Mol of Ketone The reaction was performed as described above in Example 5 except that an excess of 1.5 eq (79.8 mmol) of $ClSO_3H$ (and 1.5 eq of dioxane) was reacted with 1 eq of internal $C_{23}$-$C_{35}$ fatty ketones (53.2 mmol). Quantities of solvent $CHCl_3$ were also adjusted.

Neutralization of sulfonic acids was carried out using 1.1 eq of NaOH (10 wt %) (calculated with respect to $ClSO_3H$ amounts) in water at 60° C. during 1 hour.

No further purification was needed as under those conditions all the starting ketone was consumed. After neutralization the obtained mixture of sulfonated salts (35 wt % active matter in water) could be used as such for the preparation of the compositions of the present invention.

After evaporation of the water, 28.1 g of white solid was obtained corresponding to a quantitative isolated yield. As determined through NMR analysis, the product consisted of a mixture of 61 mol % monosulfonate and 39 mol % disulfonate.

Example 7—Sulfonation of Ketones Obtained in Example 2 With 2.1 Moles of Sulfonating Agent Per Mol of Ketone The reaction was performed as described above in Example 5 except that an excess of 2.1 eq (111.7 mmol) of $ClSO_3H$ (and 2.1 eq of dioxane) was reacted with 1 eq of internal $C_{23}$-$C_{35}$ fatty ketones (53.2 mmol). Quantities of solvent $CHCl_3$ were also adjusted.

Neutralization of sulfonic acids was carried out using 1.1 eq of NaOH (10 wt %) (calculated with respect to $ClSO_3H$ amounts) in water at 60° C. during 1 hour. No further purification was needed as under those conditions all the starting ketone was consumed. After neutralization the obtained mixture of sulfonated salts (35 wt % active matter in water) could be used as such for the preparation of the compositions of the present invention.

After evaporation of the water, 31.5 g of white solid was obtained corresponding to a quantitative isolated yield. As determined through NMR analysis, the product consisted of a mixture of 18 mol % monosulfonate and 82 mol % disulfonate Example 8—Compositions of the Present Invention Comprising (Di)Sulfonated Compounds Derived from $C_{23}$-$C_{35}$ Internal Ketones Cut The performance of surfactant formulations comprising internal ketone (di)sulfonate obtained from a cut of coconut fatty acids ($C_{12}$-$C_{18}$) with different mono to disulfonate ratio at a temperature of 60° C. was determined in two different aqueous salt solutions (brines). The two brine compositions which have been investigated are described in Table 2.

TABLE 2

Brine compositions

|  | NaCl (% by weight of total salt) | CaCl2 (% by weight of total salts) |
|---|---|---|
| Brine 1 | 100 | 0 |
| Brine 2 | 83.9 | 16.1 |

The internal ketone sulfonates were used in combination with an alkoxylated alkyl glyceryl ether of the following formula:

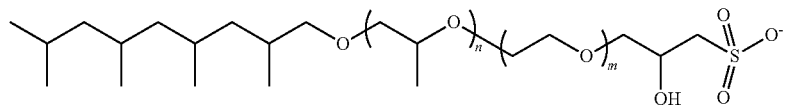

wherein n is 7 and m is 6.

The ketone sulfonates and the AAGES were used in a concentration of 4 g/L each.

Tables 3 and 4 show the solubility of the surfactant mixture in the two brines, the optimal salinity S* in the presence of dodecane as well as the approximate interfacial tension with dodecane. The optimal salinity S* corresponds to the salinity at which the interfacial tension with the oil reaches its minimum value. All experiments were performed at 60° C.

TABLE 3

Performances of the surfactant formulations in Brine 1

| Mono/Disulfonate Ratio | Formulation solubility (g/l NaCl) | S* (g/l NaCl) | IFT (mN/m) |
|---|---|---|---|
| 96/4% | Very low | No three phase behavior (WIII) | >10$^{-1}$- |
| 61/39% | 75 | 50 | <10$^{-2}$ |
| 18/82% | >90 | >90 | Not measured |

TABLE 4

Performances of the surfactant formulations in Brine 2

| Mono/Disulfonate Ratio | Formulation solubility (g/L TDS) | S* (g/l TDS) | IFT (mN/m) |
|---|---|---|---|
| 98/2% | Not soluble | — | — |
| 61/39% | 40 | 12 | <10$^{-2}$ |
| 50/50%* | 45 | 26 | <10$^{-2}$ |
| 42/58%* | >62 | 53 | <10$^{-2}$ |

S* represents the optimal salinity, IFT the interfacial tension and formulation solubility is the maximal salts concentration of the respective brine at which the surfactant mixture is soluble.

*: These ratios were obtained by blending the products 61/39 and 18/82

These results show that internal ketone sulfonate surfactants can be used to obtain optimal performances (solubility and IFT) in various brine conditions. Such mixtures can thus be very useful to match different reservoir conditions.

The optimal salinity S* in brine 2 (TDS g/l) can be easily modified and tuned by the ratio monosulfonate/disuflonate used. This ratio can be obtained directly in the synthesis by using the appropriate sulfonating agent:ketone ratio.

Example 9—Synthesis of $C_{15}$-$C_{35}$ Ketones Cut Starting from a $C_8$-$C_{18}$ Coco Saturated Fatty Acids Cut The reaction was carried under argon in a 750 mL reactor equipped with mechanical stirring, Dean Stark apparatus and an addition funnel. In the reactor, 6.8 g (0.12 mol) of iron powder were dispensed and 200 g (0.97 mol) of the coco saturated fatty acids cut (with the following distribution: $C_8$: 7 wt %, $C_{10}$: 8 wt %, $C_{12}$: 48 wt %, $C_{14}$: 17 wt %, $C_{16}$: 10 wt %, $C_{18}$: 10 wt %) was introduced into the addition funnel.

A first partial amount of 50 g of fatty acids was added into the reactor and the temperature was brought to 250° C. The mixture was stirred at this temperature during 4 h 00. During this time the color of the media changed to black and $H_2$ gas was released. FTIR analysis of the crude mixture shows complete formation of intermediate iron carboxylate complexes. The temperature was then raised to 330° C. and the mixture was stirred at this temperature during 2 h 00. During this time the intermediate iron carboxylate complexes are decomposed to fatty ketones, iron oxide and $CO_2$. The remaining fatty acids (150 g) are slowly introduced into the reactor such that the temperature of the reaction medium doesn't fall down below 320° C. and at a flow rate which allowed keeping concentration of fatty acids in the reaction media very low (for example with an addition flow rate of around 25 g fatty acids/hour).

Practically this can be done through the successive slow additions (1 hour per addition) of 3 portions of 50 g of melted fatty acids with 1 hour of stirring at 330° C. between each addition.

At the end of the last addition, the crude medium is stirred at 330° C. during 2 hours and the reaction progress is monitored through FTIR. When the reaction is completed (no more iron complex detected by FTIR), the mixture is allowed to cool down at room temperature and 400 mL of $CHCl_3$ is added to the crude media. The mixture is stirred at 40° C. in order to solubilize the product. The obtained suspension is filtered on a silica plug (400 g) and eluted using 3 L of chloroform. Evaporation of the solvent affords 161 g (0.46 mol) of the product $C_{15}$-$C_{35}$ ketones as a white wax (95% isolated yield) analytically pure.

Example 10—Sulfonation of the $C_{15}$-$C_{35}$ Ketones Cut Obtained Previously with 1.35 Moles of Sulfonating Agent Per Mol of Ketone The reactions were performed under a strictly anhydrous argon atmosphere. All the glassware was dried under vacuum at 110° C. overnight prior to the reaction. In a 500 mL round bottom flask equipped with a magnetic stirring, 40 g (113 mmol) of ketones $C_{15}$-$C_{35}$ was dissolved in 107 mL of $CHCl_3$ and the temperature of the mixture was set up at 45° C.

In another 100 mL round bottom flask, a solution of 10 mL of $ClSO_3H$ (153 mmol) dissolved in 44.5 mL of $CHCl_3$ and 13.1 mL of dioxane (153 mmol) was carefully prepared. This solution was then slowly added to the ketone solution via cannula over 3.5 hours and through 5 crops. After addition, the solvent was removed under vacuum. Then the obtained sulfonic acid was neutralized with 67 mL NaOH (10 wt %) along with an additional amount of 30 mL of water and under mechanical stirring at 60° C. during 1 hour in order to afford sodium sulfonate salts. After neutralization, the obtained mixture of sulfonated salts (around 38 wt % active matter in water) could be used as such for the preparation of the compositions of the present invention. Evaporation of water affords 56.5 g of yellow solid corresponding to a quantitative yield. As determined through NMR analysis, the product consisted of a mixture of 62 mol % monosulfonate and 38 mol % disulfonate.

Example 11—Sulfonation of the $C_{15}$-$C_{35}$ Ketones Cut Obtained Previously with 1.5 Moles of Sulfonating Agent Per Mol of Ketone The reactions were performed under a strictly anhydrous argon atmosphere. All the glassware was dried under vacuum at 110° C. overnight prior to the reaction. In a 250 mL round bottom flask equipped with a magnetic stirring, 10 g (29 mmol) of ketones $C_{15}$-$C_{35}$ was dissolved in 27 mL of $CHCl_3$ and the temperature of the mixture was set up at 45° C. In another 100 mL round bottom flask, a solution of 2.9 mL of $ClSO_3H$ (44 mmol) dissolved in 13 mL of $CHCl_3$ and 3.8 mL of dioxane (44 mmol) was carefully prepared. This solution was then slowly added to the ketone solution via cannula over 2 hours and through 4 crops. After addition, the mixture is allowed to stir at 45° C. during 2 hours and the solvent was removed under vacuum. Then the obtained sulfonic acid was neutralized with 20.5 mL NaOH (10 wt %) along with an additional amount of 7 mL of water and under mechanical stirring at 60° C. during 1 hour in order to afford sodium sulfonate salts. After neutralization, the obtained mixture of sulfonated salts (around 38 wt % active matter in water) could be used as such for the preparation of the compositions of the present invention. Evaporation of water affords 15.4 g of yellow solid corresponding to a quantitative yield. As determined through NMR analysis, the product consisted of a mixture of 47 mol % monosulfonate and 53 mol % disulfonate.

Example 12—Sulfonation of the $C_{15}$-$C_{35}$ Ketones Cut Obtained Previously with 1.7 Moles of Sulfonating Agent Per Mol of Ketone The reactions were performed under a strictly anhydrous argon atmosphere. All the glassware was dried under vacuum at 110° C. overnight prior to the reaction. In a 250 mL round bottom flask equipped with a magnetic stirring, 20 g (58 mmol) of ketones $C_{18}$-$C_{35}$ was dissolved in 54 mL of $CHCl_3$ and the temperature of the mixture was set up at 45° C. In another 100 mL round bottom flask, a solution of 6.6 mL of $ClSO_3H$ (99 mmol) dissolved in 30 mL of $CHCl_3$ and 8.4 mL of dioxane (44 mmol) was carefully prepared. This solution was then slowly added to the ketone solution via cannula over 2.5 hours and through 5 crops. After addition, the mixture is allowed to stir at 45° C. during 2 hours and the solvent was removed under vacuum. Then the obtained sulfonic acid was neutralized with 44 mL NaOH (10 wt %) along with an additional amount of 10 mL of water and under mechanical stirring at 60° C. during 1 hour in order to afford sodium sulfonate salts. After neutralization, the obtained mixture of sulfonated salts (around 38 wt % active matter in water) could be used as such for the preparation of the compositions of the present invention. Evaporation of water affords 31.3 g of yellow solid corresponding to a quantitative yield. As determined through NMR analysis, the product consisted of a mixture of 30 mol % monosulfonate and 70 mol % disulfonate.

Example 13—Compositions of the Present Invention Comprising (Di)Sulfonated Compounds Derived from $C_{15}$-$C_{35}$ Internal Ketones Cut The performance of surfactant formulations comprising internal ketone (di)sulfonate obtained from a cut of coconut fatty acids ($C_8$-$C_{18}$) with different mono to disulfonate ratio at a temperature of 60° C. was determined in two different aqueous salt solutions (brines). The two brine compositions which have been investigated are described in Table 5.

TABLE 5

| Brine compositions | | |
|---|---|---|
| | NaCl (% by weight of total salt) | CaCl2 (% by weight of total salts) |
| Brine 1 | 100 | 0 |
| Brine 2 | 83.9 | 16.1 |

The internal ketone sulfonates were used in combination with an alkoxylated alkyl glyceryl ether of the following formula:

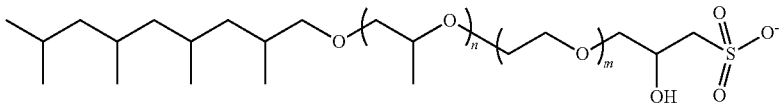

wherein n is 7 and m is 6.

The ketone sulfonates and the AAGES were used in a concentration of 4 g/L each.

Tables 6 and 7 show the solubility of the surfactant mixture in the two brines, the optimal salinity S* in the presence of dodecane as well as the approximate interfacial tension with dodecane. The optimal salinity S* corresponds to the salinity at which the interfacial tension with the oil reaches its minimum value. All experiments were performed at 60° C.

TABLE 6

Performances of the surfactant formulations in Brine 1

| Mono/Disulfonate (%) | Formulation solubility (g/l NaCl) | S* (g/l NaCl) | IFT (mN/m) |
| --- | --- | --- | --- |
| 30/70% | 80 | 145 | $5.8 \cdot 10^{-3}$ |
| 47/53% | 115 | 100 | $1.07 \cdot 10^{-3}$ |
| 50/50%* | >84 | 81 | $0.5 \cdot 10^{-3}$ |
| 62/38% | 70 | 50 | $0.34 \cdot 10^{-3}$ |

*These ratios were obtained by blending the products with 62% and 47%

The invention claimed is:

1. A process for enhanced oil recovery, the process comprising a first step of determining the salinity of an injection water and thereafter preparing a blend of internal ketone monosulfonates and disulfonates having a mixing ratio of mono- and disulfonates providing the lowest interfacial tension with the crude oil for the given salinity, wherein the blend is a mixture of 12-tricosanone monosulfonate and 12-tricosanone disulfonate in a mixture ratio of monosulfonate:disulfonate of from 1:99 to 99:1; mixing the internal ketone sulfonate mixture with the injection water and optionally further ingredients and pumping the final composition into the reservoir to recover oil from the reservoir.

2. The process according to claim 1, wherein the mixture ratio of monosulfonate:disulfonate is in the range of from 3:97 to 97:3.

3. The process according to claim 2, wherein the mixture ratio of monosulfonate:disulfonate is in the range of from 5:95 to 95:5.

* * * * *